United States Patent [19]

Mischak et al.

[11] Patent Number: 6,124,430
[45] Date of Patent: Sep. 26, 2000

[54] HUMAN BRAIN NATRIURETIC PEPTIDES

[75] Inventors: Ronald P. Mischak, Palo Alto, Calif.; Garrett A. Lim, Havertown, Pa.; Jan Marian Scardina, San Carlos, Calif.

[73] Assignee: Scios Inc., Sunnyvale, Calif.

[21] Appl. No.: 08/942,332

[22] Filed: Oct. 1, 1997

Related U.S. Application Data

[62] Division of application No. 08/610,172, Mar. 4, 1996.

[51] Int. Cl.$^7$ .................................................. C07K 14/47
[52] U.S. Cl. ......................... 530/324; 436/544; 530/327; 530/839; 530/841
[58] Field of Search ............................ 436/544; 530/324, 530/327, 839, 841

[56] References Cited

U.S. PATENT DOCUMENTS 5,114,923   5/1992   Seilhamer.

FOREIGN PATENT DOCUMENTS

| | | |
|---|---|---|
| 0542255 | 5/1993 | European Pat. Off. . |
| 05056794 | 3/1993 | Japan . |
| 05068581 | 3/1993 | Japan . |
| 05207891 | 8/1993 | Japan . |
| WO 93/24531 | 12/1993 | WIPO . |

OTHER PUBLICATIONS

Itoh et al., "Brain Natriuretic Peptide Is Present in the Human Amniotic Fluid and Secreted from Amnion Cells", (1993) *Journal of Clinical Endocrinology and Metabolism* 76:907–911.

Kambayashi et al., "Isolation and Sequence Determination of Human Brain Natiuretic Peptide in Human Atrium", (1990) *FEBS Letters* 259:341–345.

Mukoyama et al., "Human Brain Natriuretic Peptide, A Novel Cardiac Hormone", (1990) *The Lancet* 335:801–802.

Aldwin et al., "A Water–Soluble, Monitorable Peptide and Protein Crosslinking Agents" *Anal. Biochem.* 164: 494–501 (1987).

Briand "Retro–Inverso Peptidomimetics as New Immunological Probes" *J. Biol. Chem.* 270(35): 20686–20691 (1995).

Burrell et al., "A New Radioimmunoassay for Human Alpha Atrial Natriuretic Peptide and its Physiological Validation" *J. Immunoassay* 11(2): 159–175 (1990).

Chorev et al., "Recent Developments In Retro Peptides and Proteins—An Ongoing Topochemical Exploration" *TIBTECH* 13: 438–444 (1995).

Galfre et al., "Antibodies to Major Histocompatibility Antigens Produced by Hybrid Cell Lines" *Nature* 266: 550–552 (1977).

General Protocol for Radioimmunoassay Kit, Penninsula Laboratories, Inc., Belmont, CA. pp. 2–10, 1991.

Hashida et al., "Novel and Ultrasensitive Noncompetitive Enzyme Immunoassay (Hetero–Two–Site Complex Transfer Enzyme Immunoassay) for α–Human Atrial Natriuretic Peptide" *J. Clin. Lab. Anal.* 6: 201–208 (1992).

Ingwersen et al., "Superiority of Sandwich ELISA Over Competitive RIA for the Estimation of ANP–270, an Analogue of Human Atrial Natriuretic Factor" *J. Immunol. Methods* 149: 237–246 (1992).

Ishikawa et al., "Enzyme–Labeling of Antibodies and their Fragments for Enzyme Immunoassay and Immunohistochemical Staining" *J. Immunoassay* 4(3): 209–327 (1983).

Itoh, H. et al., "Preparation of Monoclonal Antibodies Against Brain Natriuretic Peptide and Their Application to Radioimmunoassay and Passive Immunization", *Endocrinology* (1990) 127: 1292–1300.

Kricka, "Selected Strategies for Improving Sensitivity and Reliability of Immunoassays" *Clin. Chem.* 40(3): 347–357 (1994).

Kricka, "Ultrasensitive Immunoassay Techniques" *Clin. Biochem.* 26: 325–331 (1993).

Mariani et al., "A New Enzymatic Method to Obtain High–Yield F(ab)$_2$ Suitable for Clinical Use From Mouse IgGL" *Mol. Immunol.* 28(1/2): 69–77 (1991).

Mathis, "Probing Molecular Interactions with Homogeneous Techniques Based on Rare Earth Cryptates and Fluorescence Energy Transfer" *Clin. Chem.* 41(9): 1391–1397 (1995).

Merrifield et al. "Retro and Retroenantio Analogs of Cecropin–Melittin Hybrids" *Proc. Natl. Acad. Sci. USA* 92: 3449–3449 (1955).

Mojsov et al., "Preproglucagon Gene Expression in Pancreas and Intestine Diversifies at the Level of Post–Translational Processing" *J. Biol. Chem.* 261(25): 11880–11889 (1986).

Motwani et al., "Plasma Brain Natriuretic Peptide As An Indicator for Angiotensin–Converting–Enzyme Inhibition After Myocardial Infarction" *Lancet* 341: 1109–1113 (1993).

Mukoyama et al. "Brain Natriuretic Peptide as a Novel Cardiac Hormone in Humans" *J. Clin. Invest.* 87: 1402–1412 (1988).

Nakagawa et al., "Preparation of a Monoclonal Antibody Against Mouse Brain Natriuretic Peptide (BNP) and Tissue Distribution of BNP in Mice" *Clin. and Exper. Pharm. and Phys.* Suppl. 1, S186–S187 (1995).

Pfeffer et al., "Effect of Captopril on Mortality and Morbidity in Patients with Left Ventricular Dysfunction After Myocardial Infarction" *New Eng. J. Med.* 327: 669–677 (1992).

(List continued on next page.)

*Primary Examiner*—Christina Y. Chan
*Assistant Examiner*—Phillip Gambel
*Attorney, Agent, or Firm*—Morrison & Foerster LLP

[57] ABSTRACT

The present invention provides reagents and assays for the quantification of hBNP in biological fluid samples such as plasma or serum. Antibodies are provided which are monospecific to epitopes comprising the amino acid sequences 5–13, 1–10 and 15–25 of hBNP. These antibodies, and peptide fragments containing these sequences, can be employed in the assays of the invention, which may be carried out in a sandwich format or a competition format.

7 Claims, 11 Drawing Sheets

OTHER PUBLICATIONS

Prowse et al., "Human Atrial Natriuretic Factor (ANF): Characterization of a Monoclonal Antibody Panel and its Use in Radioimmunoassay" *J. Immunol. Methods* 118: 91–100 (1989).

Rasmussen et al., "Solid–Phase Double–Antibody Radio–Immunoassay for Atrial Natriuretic Factor"; *Scand. J. Clin. Lab. Invest.* 50:319–324 (1990).

Richards et al., "Radio–Immunoassay for Plasma Alpha Human Atrial Natriuretic Peptide: A Comparison of Direct and Pre–Extracted Methods" *J. Hypertension* 5: 227–236 (1987).

Rosemalen et al., "A Sensitive Radioimmunoassay of Atrial Natriuretic Peptide in Human Plasma; Some Guidelines for Clinical Applications" *Z. Karkiol* 77(2): 20–25 (1988).

Sagnella et al., "Atrial Natriuretic Peptide in Human Plasma– Comparison of Radioreceptor Versus Radioimmunossay" *Clinica Chimica Acta* (1987) 166:37–33.

Sarda et al., "Radioimmunoassay for Rat B–type Natriuretic Peptide (BNP–45)" *J. Immunoassay* (1992) 14(3): 167–182.

Sudoh et al "A New Natriuretic Peptide in Porcine Brain" *Nature* 332: 78–81 (1988).

Sudoh et al., "Brain Natriuretic Peptide–32: N–Terminal Six Amino Acid Extended Form of Brain Natriuretic Peptide Identified in Porcine Brain" *Biochem. Biophys. Res. Comm.* 155(2): 726–732 (1988).

Tateyama et al., "Characterization of Immunoreactive Brain Natriuretic Peptide in Human Cardiac Atrium" *Biochem. Biophys. Res. Comm.* 166(3): 1080–1087 (1990).

Tateyama et al., "Concentration and Molecular Forms of Human Brain Natriuretic Peptide in Plasma" *Biochem. Biophys. Res. Comm.* (1992) 185(2): 760–767.

Tateyama et al., "Microenzyme Immunoassay for the Measurement of Brain Natriuretic Peptide (BNP)–like Immunoreactivity in Porcine Plasma" *J. Immun. Methods* 130: 217–222 (1990).

The SOLVD Investigators "Effect of Enalapril on Mortality and the Development of Heart Failure in Asymptomatic Patients with Reduced Left Ventricular Ejection Fractions" *New Eng. J. Med.* 327: 685–691 (1992).

Ueda et al., "Regional Distribution of Immunoreactive Brain Natriuretic Peptide in Porcine Brain and Spinal Cord" *Biochem. Biophys. Res. Comm.* 155(2): 733–739 (1988).

Undenfriend et al., "Scintillation Proximity Assay: A Sensitive and Continuous Isotopic Method for Monitoring Ligand/Receptor and Antigen/Antibody Interactions" *Anal. Biochem.* 161: 494–500 (1987).

Watanabe et al., "A Sensitive Enzyme Immunoassay for Atrial Natriuretic Polypeptide" *J. Immunol. Methods* 124: 25–28 (1989).

Yandle et al., "Assay of Brain Natriuretic Peptide (BNP) in Human Plasma: Evidence for High Molecular Weight BNP as a Major Plasma Component in Heart Failure", *J. Clin. Endocrin. and Metab.* (1993)76(4): 832–838.

Yoshibayashi et al., "Increased Plasma Levels of Brain Natriuretic Peptide in Hypertrophic Cardiomyopathy" New Eng. J. Med. 327: 434 (1992).

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 |
|---|---|---|---|---|---|---|---|---|----|----|----|----|----|----|----|----|----|----|----|----|----|----|----|----|----|----|----|----|----|----|----|
| S | P | K | M | V | Q | G | S | G | C  | F  | G  | R  | K  | M  | D  | R  | I  | S  | S  | S  | G  | L  | G  | C  | K  | V  | L  | R  | R  | H  |

FIG. 1

| PEPTIDE | POLYCLONAL Ab 4024 UNPURIFIED POLYSPECIFIC OD | POLYCLONAL Ab 4024 AFFINITY PURIFIED MONOSPECIFIC OD |
|---|---|---|
| 18-25 | 0.000 | 0.005 |
| 17-25 | 0.000 | 0.032 |
| 15-25 | 0.817 * | 0.695 * |
| 15-23 | 0.000 | 0.012 |
| 27-32 | 2.616 * | 0.000 |
| 11-17 | 0.000 | 0.005 |
| 5-13 | 2.571 * | 0.003 |
| 1-10 | 2.644 * | 0.118 |
| 1-32 | 2.667 * | 2.903 * |

* INDICATES REACTIVITY TO BNP 1-32 AND SPECIFIC EPITOPES

FIG. 2

| MAb 201.3 | |
|---|---|
| INHIBITING PEPTIDE | % INHIBITION |
| 1-32 | 92 |
| 1-15 | 80 |
| 1-10 | 89* |
| 1-8 | 33 |
| 1-6 | 29 |
| 1-4 | 0 |
| 2-10 | 0 |

| MAb 106.3 | |
|---|---|
| INHIBITING PEPTIDE | % INHIBITION |
| 1-32 | 99 |
| 1-15 | 85 |
| 3-15 | 85 |
| 5-15 | 85 |
| 5-13 | 88* |
| 5-11 | 4 |
| 7-32 | 6 |

| MAb 8.1 | |
|---|---|
| INHIBITING PEPTIDE | % INHIBITION |
| 1-32 | 99 |
| 7-32 | 90 |
| 26-32 | 88 |
| 27-32 | 85* |
| 28-32 | 5 |
| 26-31 | 1 |
| 1-31 | 1 |

* DESIGNATES THE EPITOPE SPECIFICITY FOR EACH MAb

FIG. 3

BNP LEVELS (pg/ml)

| # | CONTROL SUBJECTS | CHD PATIENTS |
|---|---|---|
| 1 | <5 | 72 |
| 2 | <5 | 1920 |
| 3 | <5 | 473 |
| 4 | 5 | 1033 |
| 5 | 14.6 | 619 |
| 6 | <5 | 304 |
| 7 | <5 | 473 |
| 8 | 5.6 | 363 |
| 9 | <5 | 416 |
| 10 | <5 | 1142 |
| 11 | <5 | 357 |
| 12 | <5 | 1215 |
| 13 | <5 | 196 |
| 14 | 21.1 | 234 |
| 15 | 7.7 | 1023 |

FIG. 11

HUMAN BRAIN NATRIURETIC PEPTIDES

This application is a division of application Ser. No. 08/610,172, filed Mar. 4, 1996.

BACKGROUND OF THE INVENTION

I. Field of the Invention

This invention relates to the field of immunoassays, more particularly to reagents and methods useful for the rapid and sensitive quantification of the peptide hormone hBNP in a biological fluid such as plasma or serum.

II. Description of the Prior Art

BNP is a cardiac derived peptide hormone that circulates in the blood and exerts potent cardiovascular and renal actions. BNP is structurally similar to two other cardiac peptides, atrial natriuretic peptide (ANP) and C-type natriuretic peptide (CNP). Porcine BNP was isolated from pig brain (Sudoh et al., Nature, 332:78–81, 1988) and, hence, was given the name "brain natriuretic peptide". In man the cardiac ventricle is the primary site of BNP synthesis. The sequence of human BNP (hBNP) was originally determined by the isolation and characterization of DNA clones from human genomic libraries (U.S. Pat. No. 5,114,923). hHBNP is synthesized, in vivo, as a 108 amino acid precursor that is enzymatically cleaved to yield the mature hBNP peptide. Mature hBNP consists of a 32 amino acid peptide containing a 17 amino acid ring structure formed by two disulfide bonds (see FIG. 1).

Elevated expression of ventricular hBNP mRNA has been reported in congestive heart failure patients as compared to normal controls. Consistent with the increase in ventricular mass and expression of BNP mRNA, hBNP levels are elevated in patients with congestive heart failure and appear to correlate with disease severity. Plasma hBNP is also believed to provide a valuable predictive marker for heart disease. Elevated plasma hBNP has been reported in heart disease, following acute myocardial infarction and during symptomless or subclinical ventricular dysfunction (Mukoyama et al., J. Clin. Invest., 87:11402–1412, 1991) (Motwani et al., Lancet, 341:1109–1113, 1993) (Yoshibayashi et al., New Eng. J. Med., 327:434, 1992). Reports from two major therapeutic trials, the SAVE trial (New Eng. J. Med., 327:669–677, 1992) and the SOLVD trial (New Eng. J. Med., 327:685–691, 1992) suggested that diagnosis and appropriate treatment of patients with asymptomatic left ventricular dysfunction could significantly reduce the incidence of fatal and non-fatal cardiovascular events and related hospitalizations.

For use in a clinical laboratory setting, it would be highly desirable to provide a diagnostic assay for hBNP which is sufficiently sensitive to measure clinically relevant titers of hBNP, sufficiently simple that it can be automated, requires a minimum amount of time to complete and preferably does not require the use of reagents having limited shelf lives. Normal levels of hBNP in plasma are quite low, on the order of 1 to 20 pg/mL. Typically, radioimmunoassays are used to measure titers in this range, although the use of radioactive reagents requires special handling, adds steps to the assay and involves the use of material having limited shelf life. A radioimmunoassay is commercially available for measuring hBNP, however, in addition to requiring the use of radioactive reagents, it is complex and cumbersome, requiring an extraction step, precipitation and several centrifugation steps, and takes several days to complete. European Patent Application No. 0 542 255 describes a radioimmunoassay for hBNP.

SUMMARY OF THE INVENTION

The present invention provides reagents and methods for the rapid and direct quantification of hBNP levels in biological fluids. The reagents and methods provided herein allow for the detection of hBNP titers at clinically relevant levels without the use of radioactive labelling (although radioactive labelling may be used, if desired). Moreover, they provide for the direct quantification of hBNP in plasma without the need for cumbersome extraction steps. The reagents and methods provided herein lend themselves readily to the automated systems used to conduct blood tests on a large scale in commercial clinical laboratories.

In one embodiment of the invention, there are provided monospecific antibodies to selected peptide epitopes within the hBNP molecule. Preferably, these monospecific antibodies are monoclonal antibodies. The monospecific antibodies of the invention are selected from the group consisting of:

(a) an antibody that is monospecific to a peptide epitope comprising amino acids 5–13 of hBNP;

(b) an antibody that is monospecific to a peptide epitope comprising amino acids 1–10 of hBNP; and (c) an antibody that is monospecific to a peptide epitope comprising amino acids 15–25 of hBNP, or functionally active fragments thereof.

A preferred antibody of the invention is a monoclonal antibody that recognizes and binds the peptide epitope comprising amino acids 5–13 of hBNP.

In another embodiment of the invention, there is provided a method for quantifying the amount of hBNP in a biological fluid using the reagents of the invention in a sandwich type immunoassay. The immunoassay may employ any of numerous labelling techniques to label and quantify immune complexes, with enzymatic labelling being preferred. This method of the invention comprises the steps of:

(a) contacting a sample of the biological fluid with a first antibody selected from the group consisting of:
 (i) an antibody that is monospecific for a peptide epitope comprising amino acids 5–13 of hBNP;
 (ii) an antibody that is monospecific for a peptide epitope comprising amino acids 1–10 of hBNP;
 (iii) an antibody that is monospecific for a peptide epitope comprising amino acids 15–25 of hBNP;
 (iv) an antibody that is monospecific for a peptide epitope comprising amino acids 27–32 of hBNP; and
 functionally active fragments of (i)–(iv), and a second antibody selected from the group consisting of:
 (i) an antibody that is monospecific for a peptide epitope comprising amino acids 5–13 of hBNP;
 (ii) an antibody that is monospecific for a peptide epitope comprising amino acids 1–10 of hBNP;
 (iii) an antibody that is monospecific for a peptide epitope comprising amino acids 15–25 of hBNP;
 (iv) an antibody that is monospecific for a peptide epitope comprising amino acids 27–32 of hBNP;
 (v) a high affinity polyclonal antibody to hBNP; and
 functionally active fragments of (i)–(v), under conditions which allow the formation of a first antibody-hBNP-second antibody complex, provided that if the first antibody is monospecific to hBNP 27-32, then the second antibody is not a polyclonal antibody;

(b) binding a quantifiable label to said second antibody, prior to, simultaneously with or after formation of the first antibody-hBNP-second antibody complex; and (c) determining the amount of hBNP in the sample by quantifying the label in the first antibody-hBNP-second antibody complex.

In other embodiments of the invention, there are provided methods for quantifying the amount of hBNP in a biological fluid using the reagents of the invention in competition type immunoassays. One such assay comprises the steps of:

(a) contacting a sample of the biological fluid with:
  (i) an antibody that is monospecific for a peptide epitope comprising amino acids 5–13 of hBNP or a functionally active fragment thereof; and
  (ii) hBNP or a fragment thereof comprising amino acids 5–13 of hBNP, having bound thereto a quantifiable label,
under conditions that allow the formation of an antibody-hBNP complex; and (b) determining the amount of hBNP in the sample by quantifying the label in the antibody-hBNP complex.

Another embodiment of the assay of the invention in a competition type format comprises the steps of:

(a) contacting a sample of the biological fluid with:
  (i) an antibody that is monospecific for a peptide epitope comprising amino acids 1–10 of hBNP or a functionally active fragment thereof; and
  (ii) hBNP or a fragment thereof comprising amino acids 1–10 of hBNP, having bound thereto a quantifiable label,
  under conditions that allow the formation of an antibody-hBNP complex; and (b) determining the amount of hBNP in the sample by quantifying the label in the antibody-hBNP complex Another embodiment of the assay of the invention in a competition type format comprises the steps of:

(a) contacting a sample of the biological fluid with:
  (i) an antibody that is monospecific for a peptide epitope comprising amino acids 15–25 of hBNP or a functionally active fragment thereof; and
  (ii) hBNP or a fragment thereof comprising amino acids 15–25 of hBNP, having bound thereto a quantifiable label,
  under conditions that allow the formation of an antibody-hBNP complex; and (b) determining the amount of hBNP in the sample by quantifying the label in the antibody-hBNP complex.

In the sandwich assays and the competition assays of the invention, the first antibody-hBNP-second antibody complex (in the case of a sandwich assay) or the antibody-hBNP complex (in the case of a competition assay) will usually be separated from the remainder of the biological fluid sample prior to quantifying the label in the complex. There are, however, known labelling techniques which allow for the direct measurement of labelled complex in the sample, i.e. without separating the complex from the sample, and such methods are considered to be within the scope of the invention. As merely exemplary of such methods, one can mention the scintillation proximity assay (Udenfriend, S. et al., *Anal. Biochem.*, 161:494–500, 1987) and the assay described in Mathis, G., *Clin. Chem.*, 41:1391–1397, 1995.

There are also provided by this invention fragments of hBNP which can be used as reagents in a competition type assay of the invention.

In one embodiment, the hBNP fragment of the invention has the formula $$X^1\text{-V-Q-G-S-G-C-F-G-R-}X^2 \text{ (SEQ ID NO: 2)} \tag{I}$$

wherein $X^1$ is selected from the group consisting of
  hydrogen.
  M-,
  K-M-,
  P-K-M- or
  S-P-K-M- (positions 1–4 of SEQ ID NO: 1);
and $X^2$ is selected from the group consisting of
  hydroxyl,
  -K,
  -K-M,
  -K-M-D; and
  -K-M-D-R (positions 14–17 of (SEQ ID NO:1);

In another embodiment, the hBNP fragment of the invention has the formula $$\text{S-P-K-M-V-Q-G-S-G-C-}X^3 \text{ (SEQ ID NO: 3)}, \tag{II}$$

wherein $X^3$ is selected from the group consisting of
  hydroxyl,
  -F and
  -F-G.

In another embodiment, the hBNP fragment of the invention has the formula $$X^4\text{-M-D-R-I-S-S-S-S-G-L-G-}X^5 \text{ (SEQ ID NO: 4)}, \tag{III}$$

wherein $X^4$ is selected from the group consisting of
  hydrogen,
  K-,
  R-K- and
  G-R-K-
and $X^5$ is selected from the group consisting of
  hydroxyl,
  -C,
  -C-K,
  -C-K-V,
  -C-K-V-L (positions 26–29of SEQ ID NO: 1);
  -C-K-V-L-R (positions 26–30of SEQ ID NO: 1);
  -C-K-V-L-R-R (positions 26–31of SEQ ID NO: 1); and
  -C-K-V-L-R-R-H (positions 26–32of SEQ ID NO: 1);

DESCRIPTION OF THE DRAWINGS

FIG. 1 is a representation of the amino acid sequence of the mature (32 amino acid) form of hBNP (SEQ ID NO:). Amino acids are represented by the standard single letter code and the solid line represents a disulfide bond between the two cysteine residues.

FIG. 2 represents the results of experiments conducted to determine the ability of rabbit polyclonal antisera raised to hBNP to bind various fragments of hBNP.

FIG. 3 represents the results of epitope mapping studies of three monoclonal antibodies designated MAb 201.3, MAb 106.3 and MAb 8.1.

FIG. 11 presents the results obtained using a competition type enzyme linked immunosorbent assay to quantify hBNP levels in the plasma of normal control subjects and subjects with congestive heart disease.

DETAILED DESCRIPTION AND PREFERRED EMBODIMENTS OF THE INVENTION

I. Antibodies of the Invention

Figure 4:
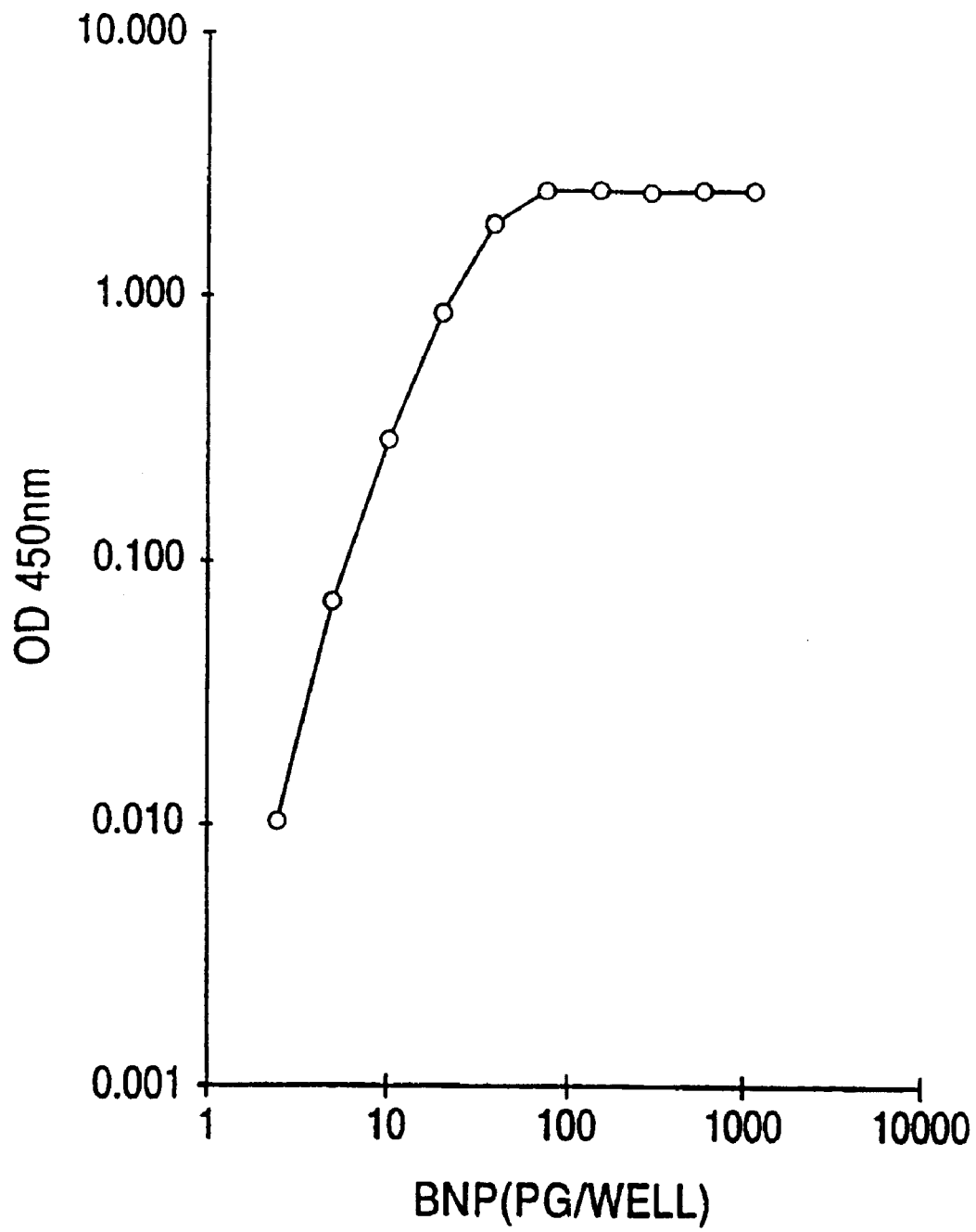
FIG. 4 is a standard curve for a sandwich type enzyme linked immunosorbent assay using MAb 106.3 as the capture antibody and a polyclonal antibody #4024 as the second antibody.

This invention provides highly sensitive reagents which allow for the rapid, simple and accurate quantification of hBNP at clinically relevant titers in biological fluids such as plasma or serum. In particular, we have identified three previously unidentified highly immunogenic epitopes within the hBNP molecule and produced antibodies monospecific to these regions. When an antibody is referred to herein as being "monospecific" to an epitope, it is meant that the antibody is capable of binding a sequence of amino acids within hBNP containing the amino acids comprising the epitope, but is incapable of binding to a sequence of amino acids within hBNP that does not contain the amino acids comprising the epitope. The monospecific antibodies of the invention are preferably, though not necessarily, monoclonal antibodies.

The three epitopes recognized by the monospecific antibodies of the invention comprise amino acids 1–10, 5–13 and 15–25 of hBNP.

Monoclonal antibodies of the invention can be produced by hybridoma cells prepared according to known procedures, e.g. Kohler, G. and Milstein, C., *Nature,* 256:495, 1975. In general, mice are immunized with an immunogenic conjugate of hBNP and a suitable partner, such as bovine serum albumin. Periodic booster injections are administered until good antibody titers are achieved. Spleen cells from the immunized mice are then fused with myeloma cells according to known procedures (i.e. Galfre et al.,*Nature,* 266:550, 1977) to produce hybridoma cells. Supernatants from the hybridoma cell cultures are screened for reactivity to hBNP. Hybridomas testing positive are recloned and their supernatants retested for reactivity. Using this procedure, as described in more detail below, we obtained hybridoma cell line 106.3, which secretes monoclonal antibodies that specifically recognize the hBNP fragment 5-13, hybridoma cell line 201.3, which secretes monoclonal antibodies that specifically recognize the hBNP fragment 1-10 and hybridoma cell line 8.1, which secretes monoclonal antibodies that specifically recognize the hBNP fragment 27-32.

Once a highly immunogenic epitope has been identified, non-monoclonal monospecific antibodies can be produced from polyclonal antisera. Polyclonal antisera is produced according to known techniques. A suitable animal, such as a rabbit, is immunized with an immunogenic conjugate of hBNP and a suitable partner. Periodic booster injections are administered until good antibody titers are achieved. By testing the antisera thus obtained for immunoreactivity against various peptide fragments of hBNP, desirable epitopes are identified. Using this procedure, we identified the peptide fragment hBNP 15-25 as a highly immunogenic epitope of hBNP. Monospecific antibodies to the identified epitope can be obtained by affinity purification of polyclonal serum on an affinity column in which a peptide fragment including only that epitope and none of the other epitopes identified in the epitope mapping is bound to a solid support. Using this general procedure, as described in more detail below, we produced non-monoclonal monospecific antibodies that specifically recognize the hBNP fragment 15-25.

It will be recognized, however, that monoclonal antibodies to this epitope can also be produced using known procedures.

Functionally active fragments of the monospecific antibodies of the invention can also be used in assays for hBNP. A functional fragment is one that retains the immunologic specificity of the antibody, although avidity and/or affinity may not be quantitatively identical. Included in the functionally active fragments are such immunoglobulin fragments as Fab, F(ab')$_2$ and Fab'. The fragments can be produced by known methods such as by enzymatic cleavage of the monospecific antibodies (see, e.g., Mariani, M. et al., *Mol. Immunol.,* 28:69–77, 1991; Ishikawa, E. et al., *J. Immunoassay,* 4:209–327, 1983).

II. Peptide Fragments of hBNP Useful in Immunoassays

In order to conduct an immunoassay in a competition type format, it is necessary to employ a labelled peptide which is capable of competing with hBNP in the biological fluid sample being assayed for binding to the antibody employed in the assay. The labelled peptide can be labelled hBNP 1-32. Using the monospecific antibodies of this invention, however, it is not necessary to employ intact hBNP 1-32 as the competing reagent. Rather, novel hBNP peptide fragments of the formulae I–III, above, can be used. In formulae I–III, amino acids are represented by their standard single-letter abbreviations. An indication that $X^1$ or $X^4$ is hydrogen means that it represents the amino-terminus of the peptide fragment. An indication that $X^2$, $X^3$ or $X^5$ is hydroxyl means that it represents the carboxy-terminus of the peptide fragment.

In particular, peptide fragments of formula I, which contain amino acids 5–13 of the hBNP sequence, can be used as reagents to compete with hBNP in the test sample for binding to an antibody of the invention that is monospecific to the epitope comprising amino acids 5–13. Peptide fragments of formula I in which $X^1$ is S-P-K-M- (positions 1–4of SEQ ID NO: 1) can be used as reagents in a competition assay employing an antibody of the invention that is monospecific to the epitope comprising amino acids 1–10.

Peptide fragments of formula II, which contain amino acids 1–10 of hBNP, can be used as reagents to compete with hBNP in the test sample for binding to an antibody of the invention that is monospecific to the epitope comprising amino acids 1–10.

Peptide fragments of formula III, which contain amino acids 15–25 of hBNP, can be employed as reagents to compete with hBNP in the test sample for binding to an antibody of the invention that is monospecific to the epitope comprising amino acids 15–25.

Additionally, one can employ, for the same purposes, peptides corresponding to the peptides of formulae I–III in which all of the amino acids have been substituted by the corresponding D-amino acids (referred to hereafter as the "D-amino acid isomers") or one can employ retro-inverso-isomers or partially modified retro-inverso-isomers of the peptides of formulae I–III. Retro-inverso-isomers are isomers in which the direction of the sequence is reversed and the chirality of each amino acid residue is inverted. Partially modified retro-inverso-isomers are isomers in which only some of the peptide bonds are reversed and the chirality of the amino acid residues in the reversed portion is inverted. Retro-inverso-isomers and partially modified retro-inverso-isomers are described by Chorev, M. and Goodman, M., *TIBTECH*, Vol. 13:438–444, 1995 These isomers have been shown to be immunologically cross-reactive with their parent peptides.

The peptide fragments of the invention can be prepared by methods known to those skilled in the art such as, for example, solid phase peptide synthesis using the procedure of Merrifield et al., (*Proc. Natl. Acad. Sci. USA*, 92:3449–3453, 1955). The retro-inverso derivatives can be prepared by the procedure of Briand et al., *J. Biol. Chem.*, 270:20686–20691, 1995.

III. Immunoassays of the Invention

The reagents of the invention can be used to carry out immunoassays to quantify hBNP levels in biological fluids such as plasma, serum and whole blood. The assays can be carried out either in a sandwich type format or in a competition format. When measuring hBNP levels in blood, the biological fluid is preferably plasma or serum, which can be prepared from whole blood using known procedures.

In a sandwich type assay, two different antibodies are employed to separate and quantify the hBNP in the biological fluid sample. The two antibodies bind to the hBNP, thereby forming an immune complex, or sandwich. Generally, one of the antibodies is used to capture the hBNP in the sample and a second antibody is used to bind a quantifiable label to the sandwich. Preferably, the antibodies chosen to carry out the sandwich type assay are selected such that the first antibody which is brought into contact with the hBNP-containing sample does not bind all or part of the epitope recognized by the second antibody, thereby significantly interfering with the ability of the second antibody to bind hBNP. Consequently, if a sandwich type format is chosen, one preferably should not employ an antibody monospecific for hBNP 5-13 in combination with an antibody monospecific for hBNP 1-10 inasmuch as the epitopes recognized by these antibodies overlap. We have found, however, that an excellent assay can be effected using a monospecific antibody as the first antibody brought into contact with the hBNP-containing sample and a high affinity polyclonal antibody for hBNP1-32 as the second antibody. In particular, we have produced a sandwich type assay which is sensitive in the range of clinically relevant hBNP titers using a monoclonal antibody which recognizes the epitope hBNP 5-13 as a capture antibody and a rabbit polyclonal antibody to hBNP as the second antibody (see Examples 9 and 10).

The fluid sample can be contacted with the first antibody and the second antibody simultaneously or sequentially. In a preferred embodiment of the sandwich assay of the invention, the hBNP-containing biological fluid sample is first brought into contact with a first antibody which is monospecific for a particular epitope under conditions which allow the formation of an antibody-hBNP complex. Preferably, the first antibody is bound to a solid support to facilitate the ultimate separation of the sandwich complex from the fluid sample. The solid supports that can be used are well known to those skilled in the art and can be, for example, polymeric materials in the form of wells, tubes or beads. The antibody can be bound to the solid support by adsorption or by covalent bonding using a chemical coupling agent, provided the coupling agent employed does not interfere with the ability of the antibody to bind hBNP. The polymeric support materials can be derivatized to allow reactivity with various functional groups on the antibody. Typically used coupling agents include maleic anhydride, N-hydroxysuccinimide and 1-ethyl-3-(3-dimethylaminopropyl)carbodiimide. In a sandwich type assay, the antibody is normally employed in amounts substantially in molar excess of the maximum amount of hBNP expected to be in the sample. Preferably, there are employed from about 0.01 nM to about 1.0 nM of antibody per mL of undiluted plasma. In practice, one may dilute the biological fluid sample in an appropriate physiologic buffer in order to achieve an acceptable molar ratio of antibody to hBNP.

After the hBNP-containing sample has been brought into contact with the first monospecific antibody, the sample is incubated to allow the formation of a first antibody-hBNP complex. Generally, incubation is carried out at or near physiologic pH, e.g. pH 6.0 to pH 8.0 at a temperature from about 4° C. to about 37° C. Incubation time is at least about 2 minutes, although incubation can be carried out for as long as 18 hours.

The first antibody-hBNP complex is contacted with the second antibody under conditions which allow formation of a first antibody-hBNP-second antibody complex. Typically, this entails incubation under conditions similar to those outlined above for the formation of the first antibody-hBNP complex. A quantifiable label is bound to the second antibody prior to, simultaneously with or after formation of the first antibody-hBNP-second antibody complex Any of the known labels conventionally used in immunoassays may be employed. These may be, for example, radioactive labels, such as $^{125}$I, enzymatic labels such as horseradish peroxidase or alkaline phosphatase, chemiluminescent labels such as acridinium esters, bioluminescent labels, fluorescent labels, thermometric labels, immuno-polymerase chain reaction labels or others. For a review of some of the more sensitive labels that can be employed in the assays of the invention, see Kricka, L. J., *Clin. Chem.*, 40(3):347–357, 1994 and Kricka, L. J., *Clin. Biochem.*, 26:325–331, 1993. The label can be bound to the antibody directly or through a coupling agent. For example, in the case of horseradish peroxidase, the second antibody can be bound to biotin, using known techniques. Following formation of the first antibody-hBNP-second antibody complex, the complex can be contacted with avidin-horseradish peroxidase, which is tightly bound by the biotin on the second antibody. An alternative method of binding the label to the second antibody involves contacting the first antibody-hBNP-second antibody complex with an antibody which recognizes and binds the $F_c$ region of the second antibody and which has the label bound thereto. Other methods of binding label to the second antibody will be readily apparent to those skilled in the art.

In a preferred embodiment, the first antibody-hBNP-second antibody complex is separated from the remainder of the biological fluid sample prior to quantification of the label. When the first antibody is bound to solid support, such as a well or a bead, separation is accomplished simply by removing the fluid from contact with the solid support. For example, the first antibody bound to a solid support may be incubated with the hBNP-containing sample to form a first antibody-hBNP complex and the fluid sample may then be removed from contact with the solid support prior to contacting the first antibody-hBNP complex with the second antibody. Alternatively, the first antibody bound to a solid support may be simultaneously contacted with the hBNP-containing sample and the second antibody to form a first antibody-hBNP-second antibody complex, followed by removal of the biological fluid from contact with the solid support.

After formation of labelled antibody-hBNP-second antibody complex and separation of the complex from the remainder of the biological fluid sample, the amount of label in the complex is quantified using known methods. For example, in the case of an enzymatic label, the labelled complex is reacted with a substrate for the label, giving a quantifiable reaction such as the development of color. Where the enzymatic label is horseradish peroxidase, for example, the labelled complex is reacted with tetramethylbenzidine (TMB), giving a reaction which can be quantified by measuring the development of color. Where the label is a radioactive label, the label is quantified using a scintillation counter. Numerous other methods are well known for quantifying the various types of labels that can be employed in the assays of the inventions. When the amount of label in the complex has been quantified, the concentration of hBNP in the biological fluid sample is determined by use of a standard curve which has been generated using serial dilutions of hBNP of known concentration.

The assay of the invention can also be carried out in a competition format. In this format, an aliquot of labelled hBNP or a suitable fragment thereof of known concentration is used to compete with the hBNP in the biological fluid for binding to hBNP monospecific antibody. In the competition assay, immobilized antibody can be simultaneously or sequentially contacted with the biological fluid sample and the labelled hBNP or hBNP fragment. The labelled hBNP or hBNP fragment, the fluid sample and the antibody are incubated under conditions similar to those indicated above in the description of the sandwich type assay. There are thus formed two species of antibody-hBNP complex, one being labelled and the other being unlabelled. The amount of label in the antibody-hBNP complex is quantified. The concentration of hBNP in the biological fluid sample can then be determined by comparing the quantity of label in the antibody-hBNP complex to a standard curve generated using serial dilutions of hBNP of known concentration. Preferably, the antibody-hBNP complex is separated from the remainder of the biological fluid sample prior to quantification of the label in the complex.

The labels which may be employed in the competition format include those previously indicated to be useful in a sandwich type assay. The label is covalently bound to the hBNP or hBNP fragment using known techniques. Commonly used techniques include the use of heterobifunctional crosslinking reagents which react with primary amines, sulfhydryls or carboxyl groups. For example, succinimidyl 4-(N-maleimidomethyl)cyclohexane-1-carboxylate can be used to bind glucose oxidase, horseradish peroxidase, β-galactosidase or alkaline phosphatase to peptides containing free sulfhydryl groups. Biotin can be conjugated to free sulfhydryl groups using BMCC, to carboxyl groups using biotin hydrazide or to amino groups using N-hydroxysuccinimide. Separation of the antibody-hBNP complex can conveniently be accomplished by binding the antibody to a solid support, such as those previously mentioned in connection with the sandwich assay format. The antibody-hBNP complex is then conveniently separated by removing the remainder of the biological fluid sample from contact with the solid support.

The labelled peptide which is used to compete with hBNP in the sample for binding to the monospecific antibody can be intact hBNP 1-32 or any peptide fragment thereof, providing the fragment contains at least that sequence of amino acids corresponding to the epitope recognized by the monospecific antibody. Thus, when the antibody employed is monospecific to the epitope comprising amino acids 1–10 of hBNP, the labelled peptide fragment can be any fragment containing at least amino acids 1–10, including, but not limited to the peptides of formula II and peptides of formula I in which $X^1$ is S-P-K-M-. When the antibody employed is monospecific to the epitope comprising amino acids 5–13 of hBNP, the labelled peptide fragment can be any fragment containing at least amino acids 5–13, including, but not limited to the peptides of formula I. When the antibody employed is monospecific to the epitope comprising amino acids 15–25 of hBNP, the labelled peptide fragment can be any fragment containing at least amino acids 15–25, including, but not limited to the peptides of formula III.

IV. Examples

The following examples are intended to further illustrate the practice of the invention and are not to be construed as limiting the scope of the invention in any way.

1. Preparation of BNP Conjugates for Antibody Production hBNP 1-32 and the fragments hBNP 1-10 and hBNP 26-32 were prepared by solid phase synthesis. These peptides were coupled to bovine serum albumin (BSA) carrier protein through a carbodiimide coupling procedure or by using the heterobifunctional cross-linking regent N-maleimido-L-aminocaproyl ester of 1-hydroxysuccinimide-2-nitro-4-benzenesulfonic acid (mal-sac-HNSA) according to the method of Aldwin and Nitecki (*Anal. Biochem.*, 164:494–501, 1987). BSA (1 mg) was reacted with 0.5 mg of the mal-sac-HNSA cross-linker in 250 μL of phosphate buffered saline (PBS) pH 7.5 for 40 minutes at room temperature. The activated BSA was purified over a G-25 Sephadex column with 0.1 M phosphate buffer pH 6.0 and combined with approximately 1 mg of the cysteine containing peptides hBNP 1-10 (SPKMVQGSGC (position 1-10 of SEQ ID NO: 1)) and hBNP 26-32 (CKVLRRH (position 26-32 of SEQ ID NO: 1)). The mixture was reacted for 4 hours at room temperature and dialyzed overnight against PBS at 4° C. A successful conjugation was indicated by the presence of a protein in an area corresponding to 75 Kd to 90 Kd on a 12% polyacrylamide gel.

BNP 1-32 BSA conjugates were prepared by dissolving approximately 1 mg BNP in 450 μL of 1 mM HCl and adding 2.8 mg of 1-ethyl-3-(3-dimethylaminopropyl) carbodiimide (EDAC). The mixture was reacted for 30 minutes on ice and added to 1.47 mg BSA in 300 μL of 5 mM NaOH. After 4 hours at room temperature, the solution was dialyzed against PBS at 4° C.

hBNP 1-32 conjugates for preparation of rabbit polyclonal antibodies were prepared by mixing 100 μg of methylated BSA (MeBSA) with 100 μg hBNP 1-32 in 100 μL PBS, pH 7.4.

2. Immunizations

For production of monoclonal antibodies, mice were immunized with peptide conjugate emulsions prepared using RIBI Adjuvant System (RIBI Immunochemical Research Inc.). About 700 μg of Synthetic Trehalose Dicorynomycolate and about 650 μg of Monophosphoryl Lipid A from *S. minnesota* R595 dissolved in 4:1 chloroform:methanol were dried in a small glass homogenizer. Sixty μL squalene was added and mixed into a paste. The peptide conjugate was then added, with continuous stirring, and an additional 1.5 mL 0.2% Tween 80 in water was added with stirring to generate a final emulsion containing approximately 1 mg/mL of protein. The emulsion was stored at 4°

C. until use. Female Balb/c mice (4 to 6 weeks old) were injected intraperitoneally with approximately 125 to 150 μg of the peptide conjugate. Mice were boosted with intraperitoneal injections once every three weeks until good titers were established. Mice received a final boost four days prior to spleen cell fusions.

For production of polyclonal antibodies rabbits were immunized with the hBNP 1-32 MeBSA conjugates. Emulsions were prepared by mixing thoroughly 100 μL of the peptide conjugate with 200 μL of Freund's Complete Adjuvant (FCA) or Freund's Incomplete Adjuvant (FIA). Three hundred μL of the FCA emulsion was injected into the inguinal lymph nodes following the method of Mojsov et al. (J. Biol. Chem., 261:11880–11889). Peptide emulsified in FIA was used for additional boosts at weeks 2 and 3. Animals were tested and bled out when titers were sufficient. Polyclonal antibodies from two animals, identified as #4024 and #4360, were employed in several of the assays described below.

3. Spleen Cell Fusions

Spleen cells were fused with the myeloma partner FOX-NY (ATCC CRL-1732) according to a method modified from Galfre et al., Nature, 266:550, 1977. Spleens were removed aseptically and single cell suspensions were prepared in serum free medium by homogenization in a 7 mL glass homogenizer. The spleen cells were washed twice prior to mixing with the myeloma partner cells. The FOX-NY:myeloma cells were harvested at log phase growth, washed and combined with the spleen cells in a 5:1 spleen:myeloma) ratio. The cells were centrifuged, medium was removed and the cell pellet was loosened by tapping. One mL of 50% polyethylene glycol (PEG) was added and stirred gently at 37° C. for approximately 2 minutes. The cells were slowly diluted with 10 mL of serum free medium, centrifuged at 400×g and resuspended in hybridoma selection medium: RPMI-1640 hybridoma medium, 10 mM Hepes, 20% fetal bovine serum, 50 U/mL penicillin, 50 μg/mL streptomycin, 75 μM adenine, 0.8 μM aminopterin and 16 μM thymidine. The cells were transferred to a T-150 culture flask and incubated overnight prior to plating in 96-well plates (about $10^5$ cells per well). Cultures were maintained at 37° C., 7% $CO_2$ in a humidified incubator. Cells were re-fed 6 days after fusion and conditioned medium was assayed for antibodies at day 10.

4. Screening and Selection

Hybridoma supernatants were tested for reactivity to hBNP 1-32 or various hBNP peptides by a standard ELISA method. Peptides, 0.1–0.5 μg/100 μL/well in PBS, were adsorbed to microtiter plates overnight at 4° C. Wells were washed with PBS/Tween (PBS containing 0.05% Tween-20) and blocked with 0.1% gelatin 1 hour at 37° C. Undiluted hybridoma supernatants (100 μL/well) were added to the peptide-coated wells for 2 hours at 37° C. Wells were washed and incubated with a goat anti-mouse IgG horseradish peroxidase conjugate diluted in PBS/Tween/ovalbumin (0.1% ovalbumin in PBS/Tween) for 2 additional hours. Another wash was followed by addition of the substrate (0.5 mg/mL O-phenylenediamine, 0.012% hydrogen peroxide in 100 mM citric phosphate buffer pH 5.0). The color reaction was stopped with 5 M sulfuric acid and absorbance read at 490 nm. An O.D. value greater than twice background was considered a positive response.

Hybridomas testing positive were recloned by limiting dilution and their supernatants retested for specific reactivity. Hybridoma and secretory stability were established by measuring growth and antibody production characteristics over several passages. This process resulted in the establishment of hybridoma cell line 106.3 and MAb 106.3, which specifically recognizes the hBNP peptide fragment 5-13, hybridoma cell line 201.3 and MAb 201.3, which specifically recognizes the hBNP peptide fragment 1-10 and hybridoma cell line 8.1 and MAb 8.1, which specifically recognizes the hBNP peptide fragment 27-32. Hybridoma cell line 106.3 was deposited at the American Type Culture Collection, 10801 University Boulevard, Manassas, Va. 20110-2209 on Feb. 14, 1996 and has accession no. HB 12044. Hybridoma cell line 201.3 was deposited at the American Type Culture Collection, 10801 University Boulevard, Manassas, Va. 20110-2209 on Feb. 14, 1996 and has accession no. HB 12045. Hybridoma cell line 8.1 was deposited at the American Type Culture Collection, 10801 University Boulevard, Manassas, Va. 20110-2209 on Feb. 21, 1996 and has the accession no. HB 12050.

5. Characterization of Antibodies

A microtiter plate ELISA was used to identify the class/subclass of the monoclonal antibodies. Mouse antibody was added to microtiter plates precoated with hBNP. Subclass specific second antibodies conjugated to horseradish peroxidase were added to detect the bound murine monoclonal antibody. Several washes followed by the addition of TMB substrate gave specific subclass reactivities for the three monoclonals. MAb 106.3 was determined to be an $IgG_{1\kappa}$ antibody, MAb 201.3 was determined to belong to subclass $IgG_{2a\kappa}$ and MAb 8.1 was determined to belong to subclass $IgG_{1\kappa}$.

Rabbit polyclonal antibody was tested for reactivity to hBNP 1-32 as well as to a variety of hBNP fragments. Microtiter plates were coated with 100 ng of the various peptides/well in 200 μL of 0.1 M bicarbonate buffer, pH 8–9. The plates were blocked with 0.1% gelatin for 30 minutes at 37° C. Rabbit serum was diluted 1:1000 followed by 5 three-fold dilutions in a Tris/Tween/BSA buffer (0.05M Tris, pH 7.5, 0.15 M NaCl, 1% BSA, 0.1% Tween-20). One hundred microliters of the antibody dilution series were added to the microtiter wells and incubated at 4° C. for 2 hours. A wash with Tris/Tween/BSA buffer was followed by a 1 hour incubation with goat anti-rabbit horseradish peroxidase. The wells were washed with buffer 4 times and 200 μL TMB substrate was added. Following a 30 to 45 minute incubation the reaction was stopped with 2.5 M sulfuric acid and the O.D. was read at 450 nm. Reactivity with the various peptides is presented in FIG. 2. The rabbit antiserum demonstrated specific reactivities with four hBNP peptide fragments, 1-10, 5-13, 15-25 and 27-32, as well as strong reactivity to hBNP 1-32.

6. Antibody Production and Purification

Hybridoma cells were seeded in roller bottles at a concentration of 300,000 cells/mL in RPMI 1640 tissue culture medium supplemented with 5% Fetal Clone (Hyclone) and grown to a density of approximately $1\times10^6$ cells/mL. The medium was replaced with serum free Hybridoma SFM medium and incubation was continued for an additional 3 to 5 days. Cells were separated from the culture medium by centrifugation at 400×g and the medium was clarified by filtration through a 0.2 μ filter. The medium was applied to a Prosep Protein-A affinity column (Bioprocessing Inc.) that had been previously equilibrated with binding buffer at pH 8.6 (1 M glycine, 0.15 M NaCl). After application of the culture medium was completed the column was washed with binding buffer until OD readings monitored at 280 nM returned to baseline levels. Antibody was eluted using 100 mM citric acid pH 3.0, concentrated to approximately 1 mg/mL in a Centriprep 10 concentrator and dialyzed overnight at 4° C. against PBS, pH 7.5. Rabbit antiserum was cleared of lipid prior to column purification of polyclonal IgG. Each 1.5 parts of serum was mixed with 1 part of SeroClear Reagent (Calbiochem), vortexed for approximately 1 minute and centrifuged to separate lipid and aqueous phases. The cleared serum was then loaded directly onto the column with a perfusion pump and purified in the same manner as the tissue culture supernatant fluid.

Rabbit antibody monospecific to the hBNP epitope comprising amino acids 15–25 was isolated from the polyclonal IgG using a diaminodipropylamine affinity column (DADPA) to which the synthetic hBNP fragment 15-27 was immobilized. The DADPA gel was prepared for coupling by washing with 5 mL water followed by 5 mL 0.1 MES buffer (2-(N-morpholino)ethanesulfonic acid), 0.9% NaCl, pH 4.7. hBNP 15-27 (2 mg) was dissolved in 2 mL of MES buffer and mixed with the gel. EDC (1-ethyl-3-(3-dimethylaminopropyl)carbodiimide) dissolved in MES buffer was added to the gel and incubated with stirring for 3 hours at room temperature. The column was washed several times with 1 M NaCl to remove unbound peptide and blocked with 0.1% ovalbumin. Prior to application of the rabbit IgG, the column was washed with 5 column volumes of PBS, pH 7.5. The rabbit IgG was cycled through the column 5 times followed by 5 washes with PBS buffer. The antibodies bound to hBNP 15-27 were eluted with 0.1 M glycine HCl, pH 2.5, brought to pH 7.5 with 2 M Tris buffer and concentrated in a Centriprep 10.

7. Preparation of Biotinylated MAbs 106.3, 201.3 and 8.1

The monoclonal antibodies were dialyzed against 0.1 M sodium borate buffer, pH 8.8 and brought to a final concentration of 1 to 3 mg/mL. Amino-hexanoyl-biotin-N-hydroxysuccinimide was prepared in dimethyl sulfoxide at a concentration of 10 mg/mL and added to the antibodies at a ratio of 200 $\mu$g of the biotin ester/mg MAb. Conjugation was carried out at room temperature for 4 hours. Uncoupled material was removed from the conjugated antibody by dialysis against phosphate buffered saline.

8. Epitope Analysis hBNP epitopes reacting with MAb 201.3, MAb 106.3 and MAb 8.1 were determined using an inhibition ELISA. hBNP biotinylated with a single biotin at the N-terminal amino acid during solid phase synthesis was used as the indicator for competition studies with MAb 106.3 and MAb 8.1. hBNP biotinylated at the two cysteine residues, 10 and 26, was prepared by coupling with the sulfhydryl reactive biotinylation reagent Biotin-BMCC. This reagent was necessary to complete the inhibition studies with MAb 201.3.

Microtiter plates were coated with goat anti-mouse IgG (F$_c$ specific) (0.5 $\mu$g/100 $\mu$L/well in bicarbonate buffer, pH 9 for 2 hours at 37° C.). Wells were washed four times with wash buffer (0.05 M Tris, pH 7.5, 0.15 M NaCl, 0.05% Tween-20). Purified monoclonal antibodies 106.3, 201.3 and 8.1 were diluted in assay buffer (0.05 M Tris, pH 7.5, 0.15 M NaCl, 0.1% Tween-20 and 1% BSA) and 180 pg/100 $\mu$L/well was incubated for 2 hours at room temperature. The wells were washed with wash buffer. Various different hBNP peptide fragments were mixed in assay buffer with biotinylated hBNP 1-32 at a molar ratio of 100:1 peptide fragment:biotin-hBNP, added to the microtiter wells and incubated for 1.5 hours at 4° C. Wells were washed once with wash buffer, streptavidin-horseradish peroxidase was added in 100 $\mu$L assay buffer and incubated for 20 minutes at 4° C. Plates were washed 4 times with wash buffer and 200 $\mu$L TMB substrate was added and incubated for 30 minutes at room temperature. Color development was stopped with 2.5 M sulfuric acid and O.D. values were read at 450 nm.

Results of the epitope analysis for MAb 106.3, MAb 201.3 and MAb 8.1 are presented in FIG. 3. The binding of biotin-hBNP 1-32 was significantly inhibited by the hBNP fragments specifically reactive with the monoclonal antibodies. For MAb 106.3, the smallest hBNP fragment capable of producing an inhibition comparable to full length hBNP 1-32 was the peptide fragment hBNP 5-13. For MAb 201.3, the smallest hBNP peptide fragment producing an inhibition comparable to that seen with hBNP 1-32 was the hBNP fragment hBNP 1-10. For MAb 8.1, the smallest hBNP peptide fragment producing an inhibition comparable to that seen with hBNP 1-32 was the fragment hBNP 27-32. Thus, hBNP fragments 1-10, 5-13 and 27-32 represent the hBNP epitopes specifically recognized by MAb 201.3, MAb 106.3 and MAb 8.1, respectively. This data also indicates that appropriate hBNP fragments, when used in a competition assay with the appropriate antibody, can provide an alternative reagent to the full length hBNP probe as an indicator of inhibition.

9. Assay for hBNP Using MAb 106.3 in a Monoclonal:Polyclonal Sandwich

Microtiter plates were coated with MAb 106.3 at 100 ng/200 $\mu$L/well in bicarbonate buffer, pH 9 and allowed to adsorb for 2 hours at 37° C. hBNP was diluted in assay buffer at 12.8 ng/mL and 2-fold serial dilutions were prepared to produce a standard curve ranging down to 12.5 pg/mL. Buffer was removed from the plates and 100 $\mu$L aliquots of the hBNP dilution series were added to the wells. Plates were incubated overnight at 4° C., washed once with wash buffer and incubated with 200 $\mu$L of a 1:2,500 dilution of rabbit antiserum containing polyclonal antibodies to hBNP. Plates were incubated for 2 hours at 37° C., washed 4 times with wash buffer and 200 $\mu$L/well goat anti-rabbit horseradish peroxidase was added. Incubation was continued at 37° C. for an additional 2 hours. Plates were washed 4 times with wash buffer, 200 $\mu$L TMB substrate was added and incubation was continued for 5 to 30 minutes. Color development was stopped with 100 $\mu$L of 2.5 M sulfuric acid and O.D. was measured at 450 nm. A standard curve was prepared by plotting O.D. versus pg/well hBNP. The standard curve is presented in FIG. 4.

10. Assay for hBNP Using MAb 201.3 in a Monoclonal:Polyclonal Sandwich

Figure 5:
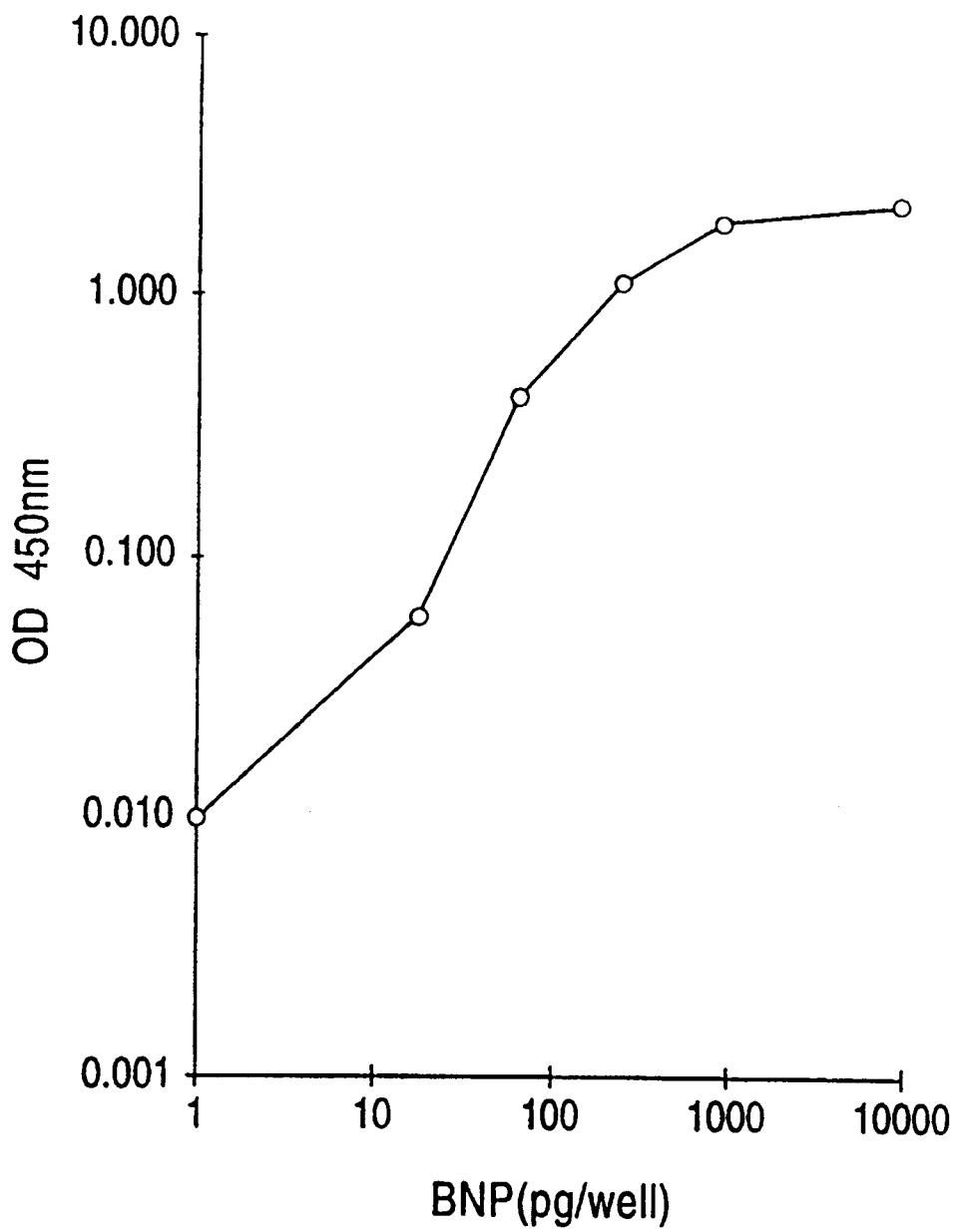
FIG. 5 is a standard curve for a sandwich type enzyme linked immunosorbent assay using MAb 201.3 as the capture antibody and polyclonal antibody #4360 as the second antibody.

Plates were coated overnight at 4° C. with 400 ng/well MAb 201.3 in bicarbonate buffer. Plates were washed with wash buffer and blocked with assay buffer for 1 hour at room temperature. hBNP was diluted in assay buffer at a concentration of 10 ng/mL and 4-fold serial dilutions were prepared to produce a standard curve ranging down to 10 $\mu$pg/mL. Plates were emptied and 100 $\mu$L aliquots of the dilution series were added to the wells. Incubation was continued at room temperature for 2 hours. The plates were washed once with wash buffer. Rabbit antiserum containing polyclonal antibodies to hBNP was diluted 1:1,000 in assay buffer, 100 $\mu$L was added to the wells and incubated at room temperature for 2 hours. After three washes with wash buffer, 100 $\mu$L/well goat anti-rabbit horseradish peroxidase was added and incubation was continued at room temperature for 1 hour. Plates were washed 3 times with wash buffer, TMB substrate was added and color was allowed to continue for 20 minutes. The reaction was stopped with 100 $\mu$L of 2.5 M sulfuric acid and O.D. was measured at 450 nm. The standard curve produced from these serial dilutions of hBNP is presented in FIG. 5.

11. Sandwich Assay Using MAb 106.3 and Monospecific Polyclonal Recognizing hBNP 15-25

Microtiter plates were coated with MAb 106.3 at 100 ng/100 $\mu$L/well in bicarbonate buffer, pH 9 overnight at 4°

Figure 6:
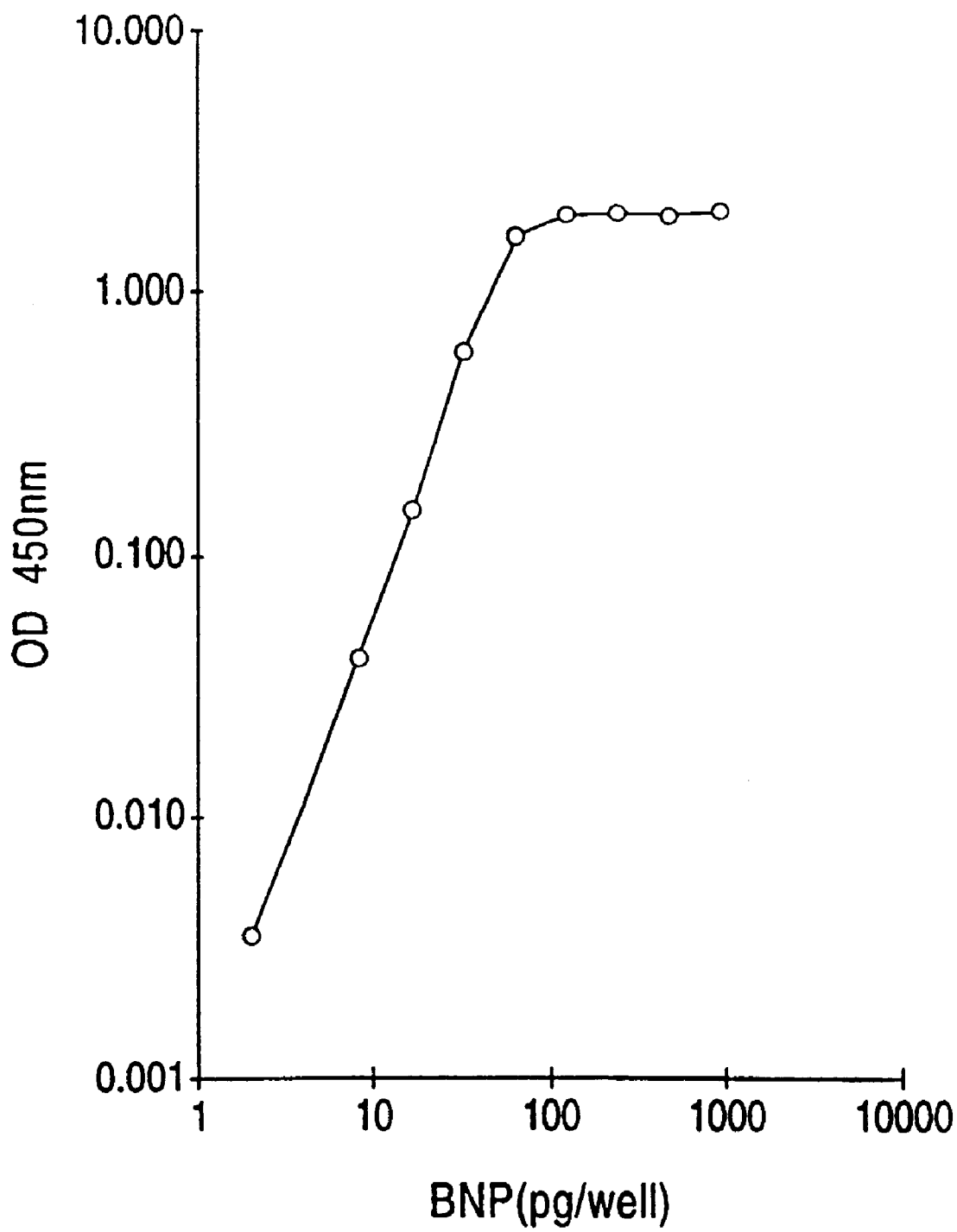
FIG. 6 is a standard curve for a sandwich type enzyme linked immunosorbent assay using MAb 106.3 as the capture antibody and a monospecific antibody against epitope 15-25 as the second antibody.

C. hBNP was diluted in assay buffer to 10 ng/mL and 2-fold serial dilutions were used to prepare a standard curve ranging down to 10 pg/mL. Plates were washed and blocked for 1 hour with assay buffer. One hundred microliter aliquots of the hBNP dilution series were added to the wells and incubated at room temperature for 2 hours. The wells were washed 4 times with wash buffer and 100 µL of a 1:50 dilution of rabbit IgG monospecific for hBNP 15-25 were added. The plates were incubated for 2 hours, washed 4 times with wash buffer and 200 µL/well of goat anti-rabbit horseradish peroxidase was added. Incubation was continued for 30 minutes. Plates were washed 4 times with wash buffer, 200 µL TMB substrate was added and color was allowed to develop for 10 minutes. Color development was stopped with 100 µL of 2.5 M sulfuric acid and O.D. was measured at 450 nm. A standard curve was prepared by plotting O.D. versus pg/well hBNP. The standard curve is presented in FIG. 6.

12. Sandwich Assay Using MAb 201.3 and Monospecific Polyclonal Recognizing hBNP 15-25

Figure 7:
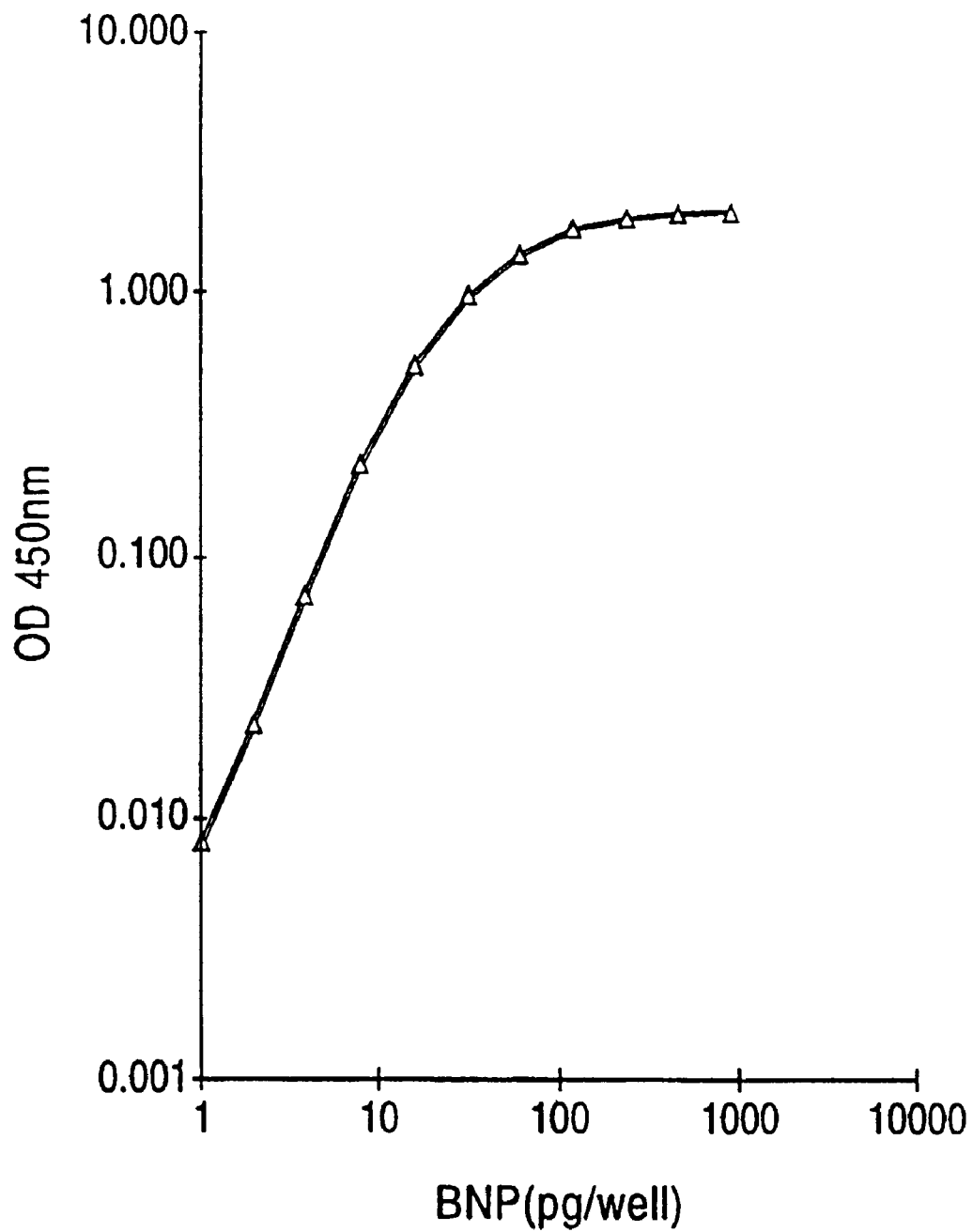
FIG. 7 is a standard curve for a sandwich type enzyme linked immunosorbent assay using MAb 201.3 as the capture antibody and a monospecific potyclonal antibody against epitope 15-25 as the second antibody.

Microtiter plates were coated with MAb 201.3 at 400 ng/100 µL/well in bicarbonate buffer, pH 9 overnight at 4° C. hBNP was diluted in assay buffer to 10 ng/mL and 2-fold serial dilutions were used to prepare a standard curve ranging down to 10 pg/mL. Plates were washed and blocked for 1 hour with assay buffer. One hundred microliter aliquots of the hBNP dilution series were added to the wells and incubated at room temperature for 2 hours. The wells were washed 4 times with wash buffer and 100 µL of a 1:50 dilution of rabbit IgG monospecific for hBNP 15-25 were added. The plates were incubated for 2 hours at room temperature, washed 4 times with wash buffer and 200 µL/well goat anti-rabbit horseradish peroxidase was added. Incubation was continued for 30 minutes. Plates were washed 4 times with wash buffer, TMB substrate was added and color was allowed to develop for 10 minutes. Color development was stopped with 100 µL of 2.5 M sulfuric acid and O.D. was measured at 450 nm. A standard curve was prepared by plotting O.D. versus pg/well hBNP. The standard curve is presented in FIG. 7.

13. Sandwich Assay for hBNP Using MAb 8.1 and MAb 106.3

Figure 8:
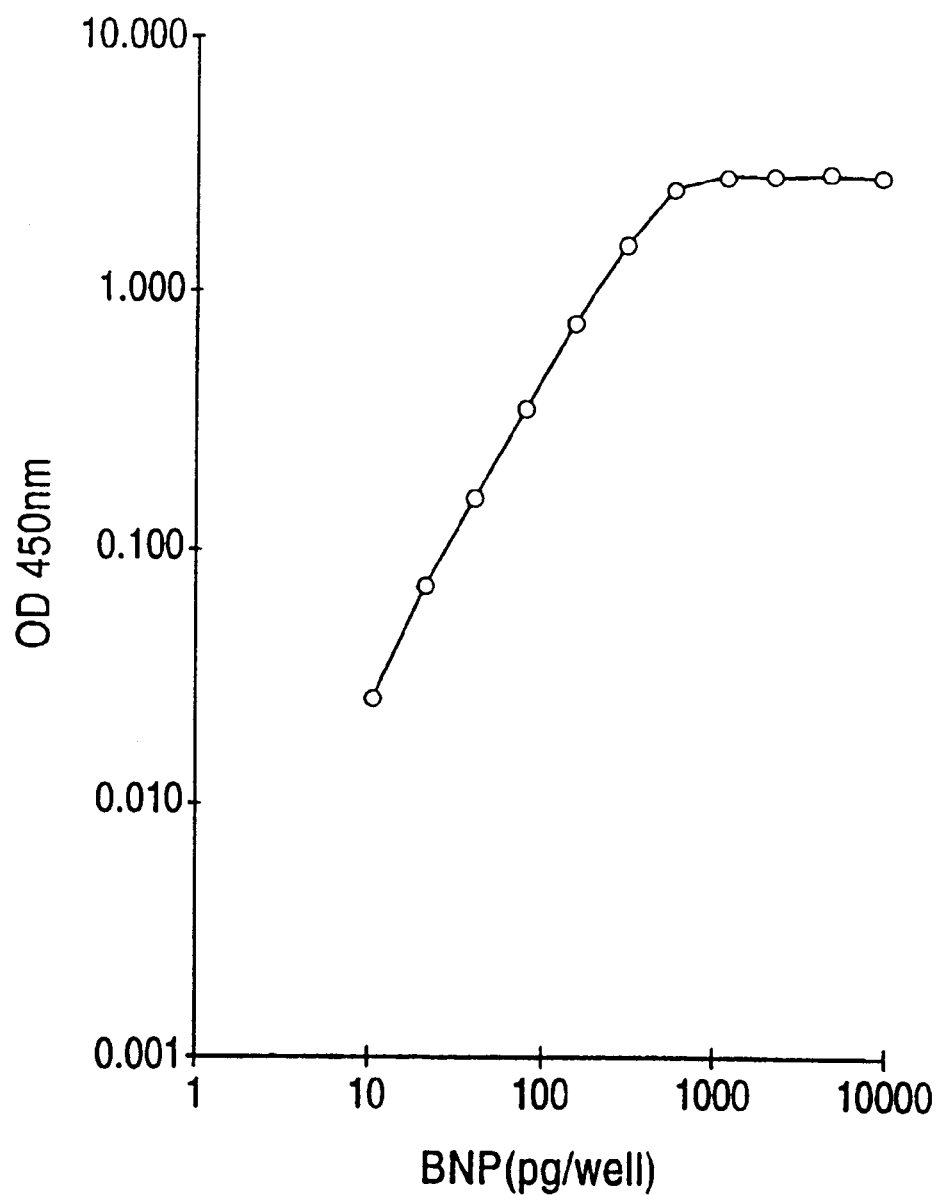
FIG. 8 is a standard curve for a sandwich type immunosorbent assay using MAb 8.1 as the capture antibody and biotinylated MAb 106.3 as the second antibody in a monoclonal:monoclonal sandwich.

Microtiter plate wells were coated overnight at 4° C. with 100 ng/well MAb 8.1 in 200 µL bicarbonate buffer. Wells were washed with wash buffer and blocked for 1 hour at 4° C. hBNP was diluted in assay buffer to 10 ng/mL and 2-fold standard dilutions were prepared to produce a standard curve ranging down to approximately 10 pg/mL. Buffer was removed from the wells and 100 µL aliquots of the hBNP standard dilution series and 100 µL of assay buffer containing 10 ng of biotinylated MAb 106.3 were added. Plates were incubated at 4° C. for 1.5 hours. Plates were washed three times with wash buffer and 200 µL of a 1:3,000 dilution of streptavidin-horseradish peroxidase was added to each well. Incubation was continued for an additional hour at 4° C. Wells were washed four times with wash buffer, 200 µL TMB substrate was added and incubation was continued for 5 to 30 minutes at room temperature. Color development was stopped with 100 µL of 2.5 M sulfuric acid and O.D. was measured at 450 nm. A standard curve was prepared by plotting O.D. versus pg/well hBNP. The standard curve is presented in FIG. 8.

14. Sandwich Assay for hBNP Using MAb 201.3 and MAb 8.1

Figure 9:
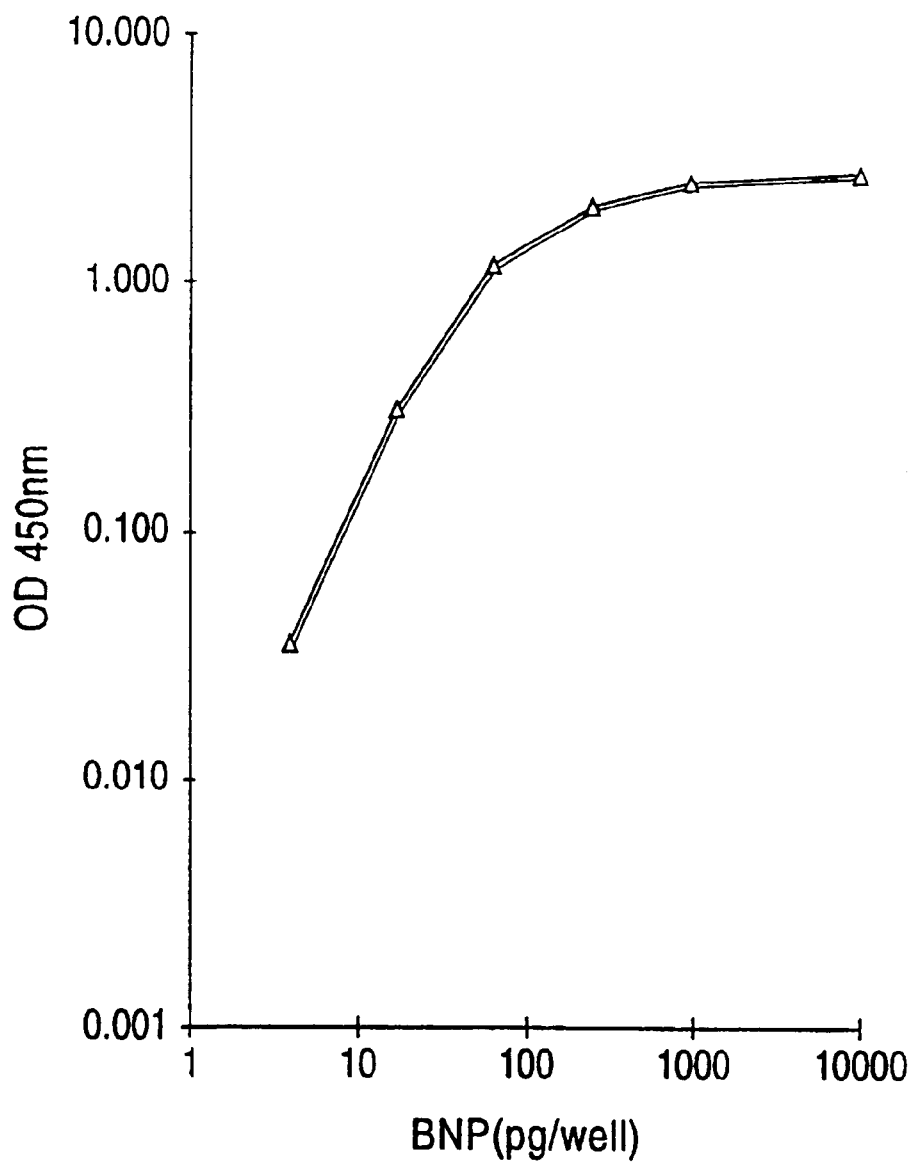
FIG. 9 is a standard curve for a sandwich type immunosorbent assay using MAb 201.3 as a capture antibody and biotinylated MAb 8.1 as a second antibody in a monoclonal:monoclonal sandwich.

Microtiter plate wells were coated overnight at 4° C. with 400 ng/well MAb 201.3 in 200 µL bicarbonate buffer. Wells were washed three times with wash buffer and blocked for 1 hour. hBNP was diluted in assay buffer to 100 ng/mL and 10 ng/mL and serial 4-fold dilutions were prepared to produce a standard curve ranging down to approximately 10 pg/mL. Buffer was removed from the wells and 100 µL aliquots of the hBNP standard dilution series were added. Incubation was carried out at room temperature for 1.5 hours. Plates were washed three times with wash buffer and 100 µL of assay buffer containing 10 ng of biotinylated MAb 8.1 was added to each well. Incubation was continued for an additional 1.5 hours at room temperature. Wells were washed three times with wash buffer and 100 µL of a 1:3,000 dilution of streptavidin-horseradish peroxidase was added to each well. Incubation was continued for an additional hour at room temperature. Wells were washed three times with wash buffer. TMB substrate (200 µL) was added and incubated at room temperature for 5 to 30 minutes. Color development was stopped with 100 µL of 2.5 M sulfuric acid and O.D. was measured at 450 nm. A standard curve was prepared by plotting O.D. versus pg/well hBNP. The standard curve is presented in FIG. 9.

15. Competition Assay Using MAb 106.3

Reagents used in this assay included MAb 106.3, biotinylated hBNP 1-32 competing reagent and a plasma diluent capable of controlling patient sample interference. Plasma diluent can be prepared from pooled human plasma or pooled human serum. Preparation from plasma involves inducement of clotting by addition of 2 mg/mL calcium chloride, incubation at room temperature to promote clotting and degrade endogenous hBNP, dialysis using 15,000 MW cutoff dialysis tubing against 0.001 M phosphate buffer containing 0.15 M NaCl, removal of clotted material, addition of EDTA at a concentration of 1.5 mg/mL and filtration through a 0.2 µ filter. Because of the susceptibility of hBNP to proteolytic degradation, it is important to add a protease inhibitor such as 4-(2-aminoethyl)-benzenesulfonyl fluoride, HCl (1 mM to the plasma diluent and assay buffer). Microtiter plates were prepared by adding 200 µL/well of goat anti-murine antibody ($F_c$ specific, approximately 0.5 µg/well) in bicarbonate buffer, pH 9 and incubating for 2 hours at 37° C. Plates were washed 4 times with wash buffer. MAb 106.3 was diluted in assay buffer and 100 µL (90 pg/well) was added to the microtiter wells. Incubation was continued for 2 hours at room temperature. Plates were emptied and 200 µL/well assay buffer was added. hBNP 1-32 was diluted directly in the plasma diluent using two-fold dilutions to produce a standard curve ranging from 320 pg/mL to 5 pg/mL. One hundred microliter samples were added to wells containing 200 µL assay buffer, plates were covered and incubated overnight at 2–8° C. on an orbital shaker. Plasma samples from patients were generally diluted at least 1:2 in plasma diluent before they were added to the wells. For patients with high levels of hBNP all further sample dilutions were prepared in plasma diluent. Following the overnight incubation, the wells were emptied and washed once with 200 µL wash buffer. Biotin-hBNP was diluted in assay buffer and 200 µL/well (125 pg/well) was added. Incubation was carried out for 1 hour at 1–8° C. on an orbital shaker. The contents were removed from the wells, 200 µL streptavidin-horseradish peroxidase was added and incubation was continued for 30 minutes at 2–8° C. The plate was washed 4–5 times with 200 µL/well wash buffer and 200 µL TMB was added. Incubation was continued at room temperature for 30 minutes to 1 hour. Color development was stopped by adding 100 µL 2.5 M sulfuric acid to the wells and O.D. measurements were made at 450 nm. O.D. values were converted to $B/B_0$ values and a standard curve was prepared by plotting $B/B_0$ versus pg/mL hBNP.

Figure 10:
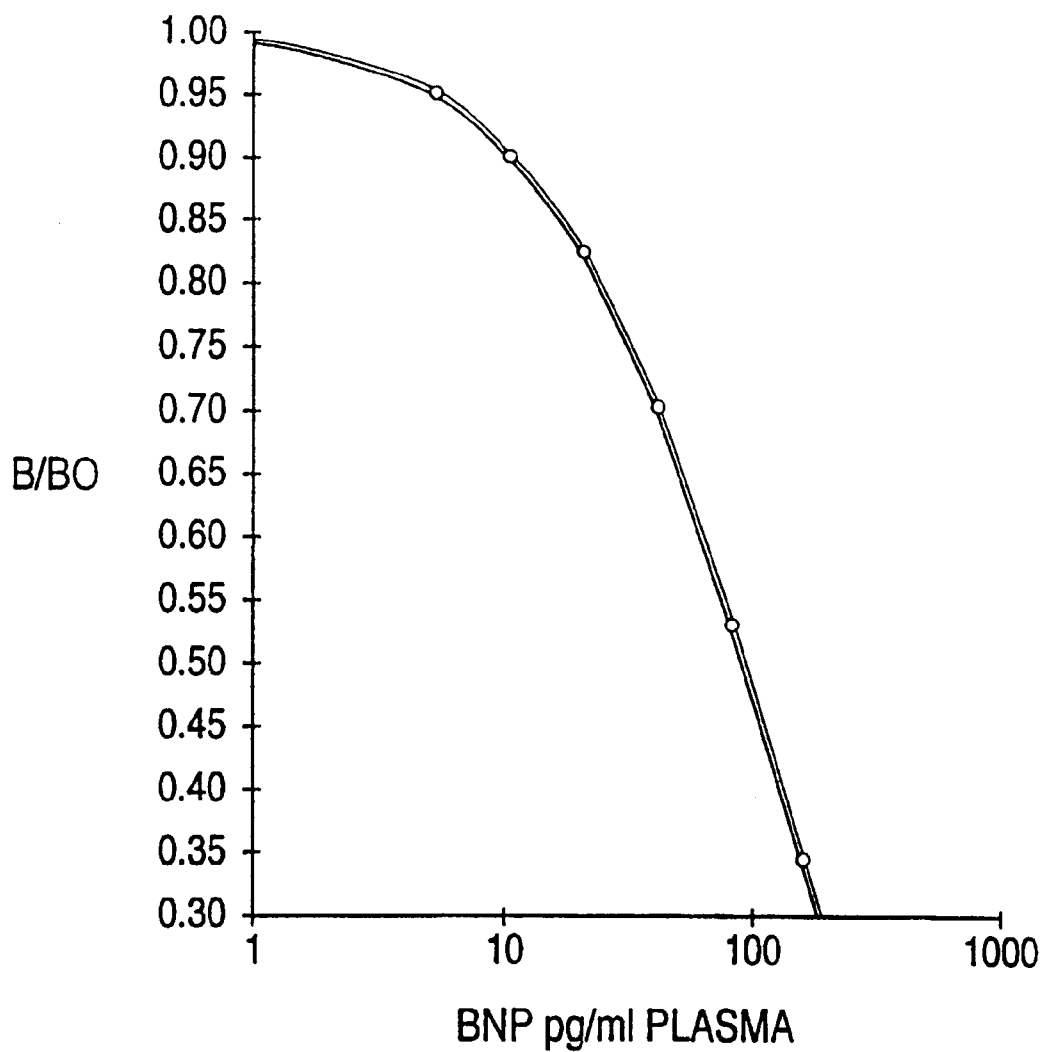
FIG. 10 is a standard curve for a competition type enzyme linked immunosorbent assay using MAb 106.3 as the antibody.

The standard curve is shown in FIG. 10. The standard curve provides a working range of ≦10 to 200 pg/mL. hBNP levels in patient samples were determined by extrapolation from the standard curve. Plasma hBNP levels determined for 15 control subjects and 15 patients with congestive heart disease are provided in FIG. 11.

We claim:

1. A peptide fragment of hBNP, useful as a reagent in an immunoassay for quantifying hBNP, the formula of which is $X^1$-V-Q-G-S-G-C-F-G-R-$X^2$ (SEQ ID NO:2), wherein $X^1$ is selected from the group consisting of
hydrogen
M-,
K-M-,
P-K-M- and
S-P-K-M- (positions 1–4 of SEQ ID NO:1)
and $X^2$ is selected from the group consisting of
hydroxyl,
-K,
-K-M,
-K-M-D and
-K-M-D-R (positions 14–17 of SEQ ID NO:1), or the retro-inverso isomers, partially modified retro-inverso-isomers or D-amino isomers thereof.

2. A peptide fragment of hBNP according to claim 1, the formula of which is

S-P-K-M-V-Q-G-S-G-C-F-G-R (positions 1–13 of SEQ ID NO:1), or the retro-inverso isomers, partially modified retro-inverso-isomers or D-amino isomers thereof.

3. A labeled peptide fragment consisting of the peptide fragment of hBNP of claim 1 bound to a quantifiable label.

4. A peptide fragment of hBNP, useful as a reagent in an immunoassay for quantifying hBNP, the formula of which is

S-P-K-M-V-Q-G-S-G-C-$X^3$ (SEQ ID NO:3), wherein $X^3$ is selected from the group consisting of
hydroxyl,
-F and
-F-G, or the retro-inverso-isomers, partially modified retro-inverso-isomers or D-amino acid isomers thereof.

5. A labeled peptide fragment consisting of the peptide fragment of hBNP of claim 4 bound to a quantifiable label.

6. A peptide fragment of hBNP, useful as a reagent in an immunoassay for quantifying hBNP, the formula of which is $X^4$-M-D-R-I-S-S-S-S-G-L-G-$X^5$ (SEQ ID NO:4), wherein $X^4$ is selected from the group consisting of
hydrogen,
K-,
R-K- and
G-R-K-
and $X^5$ is selected from the group consisting of
hydroxyl,
-C
-C-K,
-C-K-V, -C-K-V-L (positions 26–29 of SEQ ID NO: 1),
-C-K-V-L-R (positions 26–30 of SEQ ID NO: 1),
-C-K-V-L-R-R (positions 26–31 of SEQ ID NO: 1) and
-C-K-V-L-R-R-H (positions 26–32 of SEQ ID NO: 1),
or the retro-inverso-isomers, partially modified retro-inverso-isomers or D-amino acid isomers thereof.

7. A labeled peptide fragment consisting of the peptide fragment of hBNP of claim 6 bound to a quantifiable label.

* * * * *

```
                           SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 32 amino acids
         (B) TYPE: amino acid
         (C) STRANDEDNESS: single
         (D) TOPOLOGY: linear (xi) SEQUENCE DESCRIPTION: SEQ ID NO:1:

Ser Pro Lys Met Val Gln Gly Ser Gly Cys Phe Gly Arg Lys Met Asp
1               5                  10                  15

Arg Ile Ser Ser Ser Ser Gly Leu Gly Cys Lys Val Leu Arg Arg His
                20                  25                  30

(2) INFORMATION FOR SEQ ID NO:2:

(i) SEQUENCE CHARACTERISTICS:
         (A) LENGTH: 17 amino acids
         (B) TYPE: amino acid
         (C) STRANDEDNESS: single
         (D) TOPOLOGY: linear (v) FRAGMENT TYPE: internal (ix) FEATURE:
         (A) NAME/KEY: Modified-site
         (B) LOCATION: 1-4
         (D) OTHER INFORMATION: /label= X1
             /note= "Either, methionine-, lysine-methionine-,
             proline-lysine-methionine- or
             serine-proline-lysine-methionine-, or missing."

(ix) FEATURE:
         (A) NAME/KEY: Modified-site
         (B) LOCATION: 14-17
         (D) OTHER INFORMATION: /label= X2
             /note= "Either -lysine, -lysine-methionine,
             -lysine-methionine-aspartic acid or -lysine-
             methionine-aspartic acid-arginine, or missing."

(xi) SEQUENCE DESCRIPTION: SEQ ID NO:2:

Xaa Xaa Xaa Xaa Val Gln Gly Ser Gly Cys Phe Gly Arg Xaa Xaa Xaa Xaa
1               5                  10                  15

(2) INFORMATION FOR SEQ ID NO:3:

(i) SEQUENCE CHARACTERISTICS:
         (A) LENGTH: 12 amino acids
         (B) TYPE: amino acid
         (C) STRANDEDNESS: single
         (D) TOPOLOGY: linear (v) FRAGMENT TYPE: N-terminal (ix) FEATURE:
         (A) NAME/KEY: Modified-site
         (B) LOCATION: 11-12
         (D) OTHER INFORMATION: /label= X3
             /note= "Either -phenylalanine or
             -phenylalanine-glycine, or missing"
```

-continued

```
    (xi) SEQUENCE DESCRIPTION: SEQ ID NO:3:

Ser Pro Lys Met Val Gln Gly Ser Gly Cys Xaa Xaa
1               5                   10

(2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS: single
        (D) TOPOLOGY: linear (v) FRAGMENT TYPE: internal (ix) FEATURE:
        (A) NAME/KEY: Modified-site
        (B) LOCATION: 1-3
        (D) OTHER INFORMATION: /label= X4
            /note= "Either lysine-, arginine-lysine- or
            glycine-arginine-lysine- or missing "

(ix) FEATURE:
        (A) NAME/KEY: Modified-site
        (B) LOCATION: 15-21
        (D) OTHER INFORMATION: /label= X5
            /note= "Either -cysteine, -cysteine-lysine,
            -cysteine-lysine-valine, -cysteine-lysine-valine-
            leucine, -cysteine-lysine-valine-leucine-arginine,
            -cysteine-lysine-valine-leucine-arginine-arginine or
            -cysteine-lysine-valine-leucine-arginine-arginine-
            histidine or missing"

(xi) SEQUENCE DESCRIPTION: SEQ ID NO:4:

Xaa Xaa Xaa Met Asp Arg Ile Ser Ser Ser Ser Gly Leu Gly Xaa Xaa
1               5                   10                  15

Xaa Xaa Xaa Xaa Xaa
                21
```